(12) United States Patent
Ferrari et al.

(10) Patent No.: US 9,649,264 B2
(45) Date of Patent: May 16, 2017

(54) COSMETIC COMPOSITION FOR MAKING UP THE SKIN

(71) Applicant: L'OREAL, Paris (FR)

(72) Inventors: Veronique Ferrari, Maisons-Alfort (FR); Bouchra Bouarfa, Paris (FR); Gaelle Brun, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/403,630

(22) PCT Filed: Jun. 21, 2013

(86) PCT No.: PCT/EP2013/063044
§ 371 (c)(1),
(2) Date: Nov. 25, 2014

(87) PCT Pub. No.: WO2013/190112
PCT Pub. Date: Dec. 27, 2013

(65) Prior Publication Data
US 2015/0125411 A1    May 7, 2015

(30) Foreign Application Priority Data

Jun. 21, 2012 (FR) .................................... 12 55895

(51) Int. Cl.
| | | |
|---|---|---|
| *A61K 8/25* | (2006.01) | |
| *A61K 8/34* | (2006.01) | |
| *A61Q 1/02* | (2006.01) | |
| *A61K 8/81* | (2006.01) | |
| *A61K 8/29* | (2006.01) | |
| *A61K 8/19* | (2006.01) | |
| *A61K 8/895* | (2006.01) | |
| *A61K 8/31* | (2006.01) | |
| *A61K 8/891* | (2006.01) | |
| *A61K 8/26* | (2006.01) | |
| *A61K 8/87* | (2006.01) | |
| *A61K 8/88* | (2006.01) | |
| *A61K 8/91* | (2006.01) | |
| *A61K 8/06* | (2006.01) | |

(52) U.S. Cl.
CPC ................ *A61K 8/25* (2013.01); *A61K 8/064* (2013.01); *A61K 8/19* (2013.01); *A61K 8/26* (2013.01); *A61K 8/29* (2013.01); *A61K 8/31* (2013.01); *A61K 8/345* (2013.01); *A61K 8/817* (2013.01); *A61K 8/87* (2013.01); *A61K 8/88* (2013.01); *A61K 8/891* (2013.01); *A61K 8/895* (2013.01); *A61K 8/91* (2013.01); *A61Q 1/02* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 2006/0039938 A1* | 2/2006 | Josse ........................ | A61K 8/88 424/401 |
| 2010/0031969 A1* | 2/2010 | Jager Lezer ......... | A45D 40/262 132/200 |
| 2010/0158832 A1* | 6/2010 | Chodorowski-Kimmes ............................ | A61K 8/8194 424/59 |

FOREIGN PATENT DOCUMENTS

GB    2 404 588    2/2005

OTHER PUBLICATIONS

Dow Corning, "Dow Corning VM-2270 Aerogel Fine Particle", Jul. 12, 2007.*
Evonik, "Aerosil R812 Product Information", Aug. 2013.*
International Search Report Issued Sep. 25, 2013 in PCT/EP13/063044 Filed Jun. 21, 2013.

* cited by examiner

*Primary Examiner* — Jianfeng Song
(74) *Attorney, Agent, or Firm* — Oblon, McClelland, Maier & Neustadt, L.L.P.

(57) ABSTRACT

The invention relates to a fluid cosmetic skin makeup composition comprising, in a physiologically acceptable medium: (i) at least one continuous oil phase, (ii) at least one sebum-pump filler and pulverulent dyestuffs, (iii) at least one hydrophobic film-forming polymer, and (iv) at least one lipophilic gelling agent which is preferably particulate, the said particulate gelling agent also possibly being a sebum pump, characterized in that the composition comprises a solids content of greater than or equal to 15% and in particular greater than or equal to 20%. The composition according to the invention is comfortable on application and has improved color remanence, especially in the presence of sebum and/or sweat.

17 Claims, No Drawings

COSMETIC COMPOSITION FOR MAKING UP THE SKIN

The invention relates to a fluid cosmetic skin makeup composition with improved colour remanence, especially with respect to sebum and/or sweat.

This composition is particularly suited to skin with increased secretion of sebum in the course of the day (combination skin to greasy skin, in particular greasy skin) and to skin that is subject to extreme temperature and/or humidity conditions, as is the case especially in Latin American and Asian countries, or to hot temperature conditions, as is the case in Southern European and North African countries.

Cosmetic compositions, for instance foundations, are commonly used to give the skin, especially the face, a colour and an aesthetic effect. These makeup products generally contain oils, pigments, fillers and optionally additives such as cosmetic or dermatological active agents. One of the problems facing consumers is that the makeup result obtained with the makeup product should last throughout the day without being freshened: once applied to the skin, this product should have good remanence properties, in particular good remanence of the colour, the mattness and the homogeneity.

To improve this remanence, polymers that afford remanence in the course of the day are generally used. These polymers are of very different chemical nature and are conveyed either in a fatty phase or in an aqueous phase (for example silicone resins, polyacrylates, latices, etc.). However, although these polymers do indeed afford remanence properties, in particular transfer resistance, they still do not provide colour remanence throughout the day (problem of remanence with respect to the secretion of sebum and water).

This remanence problem is even more pronounced when the skin is greasy and/or when the exterior temperature or humidity conditions are extreme. The makeup must then be very resistant and the use of polymers alone proves to be insufficient. There is thus still a need for cosmetic skin makeup compositions that have resistant mattness and mattness remanence and/or colour remanence under hot and/or humid atmospheric conditions.

The Applicant has observed that the use of a sebum pump and of a particulate lipophilic gelling agent, in particular a modified clay and/or hydrophobic silica aerogel particles, in a coloured hydrophobic fluid composition characterized by a high solids content, makes it possible to satisfy this need.

According to a first aspect, the invention thus relates to a fluid cosmetic skin makeup composition comprising, in a physiologically acceptable medium:
(i) at least one continuous oil phase,
(ii) at least one sebum-pump filler and pulverulent dyestuffs,
(iii) at least one hydrophobic film-forming polymer, and
(iv) at least one lipophilic gelling agent which is preferably particulate, the said particulate gelling agent also possibly being a sebum pump,
characterized in that the composition comprises a solids content of greater than or equal to 15% and in particular greater than or equal to 20%.

Solids Content

For the purposes of the present invention, the "solids content" denotes the content of non-volatile matter.

The solids content (abbreviated as SC) of a composition according to the invention is measured using a "Halogen Moisture Analyzer HR 73" commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

$$\text{Solids content(expressed as weight percentage)} = 100 \times (\text{dry mass/wet mass}).$$

In particular, a composition of the invention is characterized by a high content of volatile solvents, in particular greater than or equal to 60% by weight, especially greater than or equal to 65% by weight, relative to the total weight of the said composition, and a content of non-volatile matter of greater than or equal to 15% by weight and especially greater than or equal to 20% by weight relative to the total weight of the said composition.

The term "volatile solvents" especially means C1-C5 monoalcohols, water and volatile oils as defined below.

The term "non-volatile matter" especially means glycols and polyols, surfactants, non-volatile oils, pasty compounds, and compounds that are solid at room temperature, such as fillers, pigments, fibres, waxes, etc.

Advantageously, the composition, after application, gives a dry, powdery feel that is particularly sought by consumers who have greasy skin and/or whose skin is subject to hot and/or humid atmospheric conditions.

The term "fluid" means a composition that flows under its own weight at room temperature.

Advantageously, a composition according to the invention may have a viscosity, measured at 25° C. and at a shear rate of 200 $\text{min}^{-1}$, ranging from 0.5 to 5 Pa·s, in particular from 1 to 4 Pa·s and especially from 1.5 to 4 Pa·s. Preferably, the viscosity will range from 0.5 to 5 Pa·s, in particular from 1 to 3 Pa·s and especially from 1.5 to 2.5 Pa·s.

The viscosity is measured at 25° C. using a Contraves TV viscometer equipped with a No. 3 spindle, the measurement being performed after rotating the spindle for 10 minutes (at the end of which time stabilization of the viscosity and of the rotational speed of the spindle are observed), at a shear rate of 200 $\text{min}^{-1}$.

According to a first embodiment, a composition of the invention is an anhydrous composition, in particular an anhydrous foundation.

According to another embodiment, a composition of the invention is a water-in-oil (W/O) emulsion, in particular a W/O foundation.

According to another aspect, the invention relates to a cosmetic skin makeup process comprising the application to the skin of a composition as defined in the invention.

According to a particular mode, the composition is applied to greasy skin and/or to skin that is subject to hot and/or humid atmospheric conditions.

The invention also relates to the cosmetic use of a combination of a sebum pump and of a lipophilic gelling agent that is preferably particulate, in a cosmetic composition comprising a continuous oil phase, pulverulent dyestuffs and a hydrophobic film-forming polymer, as an agent for improving the colour and/or mattness remanence with respect to sebum and/or sweat.

Fillers with Absorbing and/or Adsorbing Power, Known as "Sebum-Pump Fillers"

A composition according to the invention comprises at least one filler with capacity for absorbing and/or adsorbing an oil or a liquid fatty substance, for instance sebum (from the skin), also known as a "sebum-pump filler".

In particular, the said filler used according to the invention has an oil absorption capacity of greater than or equal to 1 ml/g.

This oil-absorbing filler may also advantageously have a BET specific surface area of greater than or equal to 300 $m^2/g$, preferably greater than 500 $m^2/g$ and preferentially greater than 600 $m^2/g$, and especially less than 1500 $m^2/g$.

The BET specific surface area is determined according to the BET (Brunauer-Emmet-Teller) method described in the Journal of the American Chemical Society, vol. 60, page 309, February 1938 and corresponding to the international standard ISO 5794/1 (appendix D). The BET specific surface area corresponds to the total specific surface area (thus including micropores) of the powder.

The filler under consideration according to the invention is thus characterized in that it has an oil uptake of greater than or equal to 1 ml/g, especially greater than or equal to 1.5 ml/g, especially ranging from 1.5 ml/g to 20 ml/g, or even ranging from 1.5 ml/g to 15 ml/g. It preferably has an oil uptake of greater than or equal to 2 ml/g, especially ranging from 2 ml/g to 20 ml/g, or even ranging from 2 ml/g to 15 ml/g.

This oil uptake, which corresponds to the amount of oil absorbed and/or adsorbed by the filler, may be characterized by measuring the wet point according to the method described below.

Method for Measuring the Oil Uptake of a Filler:

The oil uptake of a powder is measured according to the method for determining the oil uptake of a powder as described in standard NF T 30-022. It corresponds to the amount of oil adsorbed onto the available surface of the filler, by measuring the wet point.

An amount m (in grams) of powder of between about 0.5 g and 5 g (the amount depends on the density of the powder) is placed on a glass plate and isononyl isononanoate is then added dropwise.

After addition of 4 to 5 drops of isononyl isononanoate, the isononyl isononanoate is incorporated into the filler using a spatula, and addition of the isononyl isononanoate is continued until conglomerates of isononyl isononanoate and powder have formed. From this point, the isononyl isononanoate is added one drop at a time and the mixture is then triturated with the spatula. The addition of isononyl isononanoate is stopped when a firm, smooth paste is obtained. This paste must be able to be spread over the glass plate without cracks or the formation of lumps. The volume Vs (expressed in ml) of isononyl isononanoate used is then noted.

The oil uptake corresponds to the ratio Vs/m.

The oil-uptake filler under consideration according to the invention may be of organic or mineral nature.

In particular, a composition of the invention comprises a sebum-pump filler chosen from silicas, silica sylylates (in particular hydrophobic silica aerogels), polyamide powders (in particular Nylon-6), acrylic polymer powders, especially polymethyl methacrylate, polymethyl methacrylate/ethylene glycol dimethacrylate, polyallyl methacrylate/ethylene glycol dimethacrylate or ethylene glycol dimethacrylate/lauryl methacrylate copolymer powders; perlites; magnesium carbonate, silicone filler and mixtures thereof.

In particular, a composition of the invention comprises a sebum-pump filler chosen from silicas, silica sylylates (in particular hydrophobic silica aerogels), acrylic polymer powders, especially polymethyl methacrylate, polymethyl methacrylate/ethylene glycol dimethacrylate, polyallyl methacrylate/ethylene glycol dimethacrylate or ethylene glycol dimethacrylate/lauryl methacrylate copolymer powders; perlites; magnesium carbonate, silicone filler and mixtures thereof.

A person skilled in the art will select from among the abovementioned materials the filler(s) having an oil uptake of greater than or equal to 1 ml/g, in particular greater than or equal to 1.5 ml/g and preferably greater than or equal to 2 ml/g and which are, in this respect, suitable for use in the invention.

Advantageously, the oil-absorbing powder may be a powder coated with a hydrophobic treatment agent.

The hydrophobic treatment agent may be chosen especially from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, mineral waxes, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above especially denotes an alkyl group containing from 1 to 30 carbon atoms and preferably containing from 5 to 16 carbon atoms.

Examples of fillers in accordance with the invention, i.e. having an oil uptake of greater than or equal to 1 ml/g and in particular 1.5 ml/g, are described below, with their oil uptake value measured according to the protocol described previously.

Silica powders that may be mentioned include:
porous silica microspheres, especially those sold under the names Sunsphere® H53 and Sunsphere® H33 (oil uptake equal to 3.70 ml/g) by the company Asahi Glass; MSS-500-3H by the company Kobo;
polydimethylsiloxane-coated amorphous silica microspheres, especially those sold under the name SA Sunsphere® H33 (oil uptake equal to 2.43 ml/g),
silica silylate powders, especially those sold under the name Dow Corning VM-2270 Aerogel Fine Particles by the company Dow Corning (oil uptake equal to 10.40 ml/g),
amorphous hollow silica particles, especially those sold under the name Silica Shells by the company Kobo (oil uptake equal to 5.50 ml/g),
precipitated silica powders surface-treated with a mineral wax, such as precipitated silica treated with a polyethylene wax, and especially those sold under the name Acematt OR 412 by the company Evonik-Degussa (oil uptake equal to 3.98 ml/g).

Acrylic polymer powders that may be mentioned include:
porous polymethyl methacrylate/ethylene glycol dimethacrylate spheres sold under the name Microsponge 5640 by the company Cardinal Health Technologies (oil uptake equal to 1.55 ml/g),
ethylene glycol dimethacrylate/lauryl methacrylate copolymer powders, especially those sold under the name Polytrap® 6603 from the company Dow Corning (oil uptake equal to 6.56 ml/g).

Polyamide powders that may be mentioned include:
Nylon-6 powder, especially the product sold under the name Pomp610 by the company UBE Industries (oil uptake equal to 2.02 ml/g).

A perlite powder that may especially be mentioned is the product sold under the name Optimat 1430 OR by the company World Minerals (oil uptake equal to 2.4 ml/g).

A magnesium carbonate powder that may especially be mentioned is the product sold under the name Tipo Carbomagel by the company Buschle & Lepper (oil uptake equal to 2.14 ml/g).

A silicone filler may be chosen from:
organopolysiloxane powders, preferably coated with silicone resin;
hollow hemispherical particles of silicone, and a mixture thereof.

In a preferred embodiment, the silicone filler is an organopolysiloxane powder, preferably coated with silicone resin.

The organopolysiloxane powder may especially be coated with silsesquioxane resin, as described, for example, in patent U.S. Pat. No. 5,538,793. Such elastomeric powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer. In particular, mention may be made especially of KSP-100 (oil uptake equal to 1.48 ml/g).

The hollow hemispherical particles of silicone may be NLK 500, NLK 506 and NLK 510 from Takemoto Oil and Fat. In particular, mention may be made especially of NLK 506 (oil uptake equal to 1.66 ml/g).

The oil-absorbing filler that is particularly preferred is a silica powder and more particularly a silica powder with an oil uptake at least equal to 3.70 ml/g, and especially the products sold under the name Sunsphere® H33 by the company Asahi Glass and under the name Dow Corning VM-2270 Aerogel Fine Particles by the company Dow Corning.

The filler(s) with an oil uptake of greater than or equal to 1 ml/g and in particular greater than or equal to 1.5 ml/g, otherwise known as sebum-pump fillers according to the invention, may be present in a composition according to the invention in a content ranging from 0.5% to 20% by weight, preferably from 1% to 10% by weight and better still from 1% to 6% by weight, relative to the total weight of the composition.

Lipophilic gelling agent or thickener which is preferably particulate

The term "lipophilic gelling agent or thickener" means an agent, mineral or organic, in a particulate form or not, able to gelling the oils of the composition.
The term "particulate lipophilic gelling agent or thickener" means a lipophilic gelling agent or thickener in the form of particles or of crystals (particulate or crystalline).

The composition according to the invention comprises at least one lipophilic gelling agent which is preferably particulate.
It may be mineral or organic.
In a preferable embodiment, the lipophilic gelling agent or thickener is particulate.
The lipophilic gelling agent according to the invention may be chosen from:
organomodified clays, which are clays treated with compounds chosen especially from quaternary amines and tertiary amines. Organomodified clays that may be mentioned include organomodified bentonites, such as the product sold under the name Bentone 34 by the company Rheox, and organomodified hectorites such as the products sold under the names Bentone 27 and Bentone 38 by the company Rheox. Mention may be made especially of modified clays such as modified magnesium silicate (Bentone gel VS38 from Rheox), modified hectorites such as hectorite modified with a $C_{10}$ to $C_{22}$ fatty acid ammonium chloride, for instance hectorite modified with distearyldimethylammonium chloride, for instance the product sold under the name Bentone 38V® by the company Elementis or the product sold under the name Bentone 38 CE by the company Rheox, or the product sold under the name Bentone Gel V5 5V by the company Elementis;
hydrophobic fumed silicas, which may be obtained by modification of the surface of the silica via a chemical reaction that generates a reduction in the number of silanol groups, these groups possibly being substituted especially with hydrophobic groups. The hydrophobic groups can be:
trimethylsiloxyl groups, which are obtained especially by treating fumed silica in the presence of hexamethyldisilazane. Silicas thus treated are known as "Silica silylate" according to the CTFA (6th edition, 1995). They are sold, for example, under the references Aerosil R812® by the company Degussa and Cab-O-Sil TS-530® by the company Cabot.
dimethylsilyloxyl or polydimethylsiloxane groups, which are obtained especially by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.
hydrophobic silica aerogels, such as the products sold under the name VM-2260 (INCI name: Silica silylate) by the company Dow Corning, the particles of which have a mean size of about 1000 microns and a specific surface area per unit of mass ranging from 600 to 800 $m^2/g$; mention may also be made of the aerogels sold by the company Cabot under the references Aerogel TLD 201, Aerogel OGD 201, Aerogel TLD 203, Enova® Aerogel MT 1100, Enova Aerogel MT 1200;
and mixtures thereof.

According to another embodiment, use may be made, as particulate (crystalline) lipophilic thickener, of waxes of animal, plant, mineral or synthetic origin and mixtures thereof; mention may be made of waxes of animal origin such as beeswax, spermaceti, lanolin wax and lanolin derivatives, plant waxes such as carnauba wax, candelilla wax, ouricury wax, Japan wax, cocoa butter, cork fibre wax or sugarcane wax; mineral waxes, for example paraffin wax, petroleum jelly wax, lignite wax, microcrystalline waxes or ozokerites; synthetic waxes, including polyethylene waxes, and the waxes obtained by Fischer-Tropsch synthesis; silicone waxes, in particular substituted linear polysiloxanes; examples that may be mentioned include polyether silicone waxes, alkyl or alkoxy dimethicones containing from 16 to 45 carbon atoms, alkyl methicones such as the $C_{30}$-$C_{45}$ alkyl methicone sold under the trade name AMS C 30 by the company Dow Corning; hydrogenated oils that are solid at 25° C. such as hydrogenated castor oil, hydrogenated jojoba oil, hydrogenated palm oil, hydrogenated tallow, hydrogenated coconut oil and fatty esters that are solid at 25° C. such as the $C_{20}$-$C_{40}$ alkyl stearate sold under the trade name Kester Wax K82H by the company Koster Keunen, and/or mixtures thereof.

In particular, a composition according to the invention is characterized in that the particulate lipophilic gelling agent is chosen from organomodified clays, in particular organomodified bentonites and organomodified hectorites, hydrophobic fumed silicas and hydrophobic silica aerogels; and mixtures thereof.

According to a first particular embodiment of the invention, the particulate lipophilic gelling agent is chosen from organomodified clays.

According to another particular embodiment of the invention, the particulate lipophilic gelling agent is chosen from hydrophobic silica aerogel particles.

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York, Academic Press, 1990.

The hydrophobic silica aerogel particles used in the present invention have a specific surface area per unit of mass ($S_M$) ranging from 500 to 1500 m²/g, preferably from 600 to 1200 m²/g and better still from 600 to 800 m²/g, and a size expressed as the volume-mean diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as volume-mean diameter (D[0.5]) ranging from 1 to 30 µm, preferably from 5 to 25 µm, better still from 5 to 20 µm and even better still from 5 to 15 µm.

The specific surface area per unit of mass can be determined by the nitrogen absorption method, known as the BET (Brunauer-Emmet-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the silica aerogel particles can be measured by static light scattering using a commercial particle size analyser of MasterSizer 2000 type from Malvern. The data are processed on the basis of the Mie scattering theory. This theory is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to one advantageous embodiment, the hydrophobic silica aerogel particles used in the present invention have a specific surface area per unit of mass ($S_M$) ranging from 600 to 800 m²/g and a size expressed as the volume-mean diameter (D[0.5]) ranging from 5 to 20 µm and even better still from 5 to 15 µm.

The silica aerogel particles used in the present invention may advantageously have a tapped density ρ ranging from 0.02 g/cm³ to 0.10 g/cm³, preferably from 0.03 g/cm³ to 0.08 g/cm³ and in particular from 0.05 g/cm³ to 0.08 g/cm³.

In the context of the present invention, this density may be assessed according to the following protocol, known as the tapped density protocol:

40 g of powder are poured into a measuring cylinder; the measuring cylinder is then placed on the Stay 2003 machine from Stampf Volumeter; the measuring cylinder is subsequently subjected to a series of 2500 tapping actions (this operation is repeated until the difference in volume between 2 consecutive tests is less than 2%); and then the final volume Vf of tapped powder is measured directly on the measuring cylinder. The tapped density is determined by the ratio m/Vf, in this instance 40/Vf (Vf being expressed in cm³ and m in g).

According to one preferred embodiment, the hydrophobic silica aerogel particles used in the present invention have a specific surface area per unit of volume $S_v$ ranging from 5 to 60 m²/cm³, preferably from 10 to 50 m²/cm³ and better still from 15 to 40 m²/cm³.

The specific surface area per unit of volume is given by the relationship: $S_v = S_M \times \rho$ where ρ is the tapped density expressed in g/cm³ and $S_M$ is the specific surface area per unit of mass expressed in m²/g, as defined above.

Preferably, the hydrophobic silica aerogel particles according to the invention have an oil absorption capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The aerogels used according to the present invention are hydrophobic silica aerogels, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles modified at the surface by silylation, reference may be made to the document U.S. Pat. No. 7,470,725.

Use will preferably be made of hydrophobic silica aerogel particles surface-modified with trimethylsilyl groups.

As hydrophobic silica aerogels that may be used in the invention, an example that may be mentioned is the aerogel sold under the name VM-2260 or VM-2270 (INCI name: Silica silylate) by the company Dow Corning, the particles of which have a mean size of about 1000 microns and a specific surface area per unit of mass ranging from 600 to 800 $m^2/g$.

Mention may also be made of the aerogels sold by the company Cabot under the references Aerogel TLD 201, Aerogel OGD 201 and Aerogel TLD 203, ENOVA® Aerogel MT 1100 and Enova Aerogel MT 1200.

Use will preferably be made of the aerogel sold under the name VM-2270 (INCI name: Silica silylate), by the company Dow Corning, the particles of which have an average size ranging from 5-15 microns and a specific surface area per unit of mass ranging from 600 to 800 $m^2/g$.

In another embodiment, the lipophilic gelling agent may be organic, particulate or not. Non-limiting illustrations of such materials that may especially be considered are organopolysiloxane elastomers.

The term "organopolysiloxane elastomer" means a supple, deformable organopolysiloxane with viscoelastic properties and especially the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolyzable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

In particular, the organopolysiloxane elastomer may be obtained by reaction of dimethylpolysiloxane containing dimethylvinylsiloxy end groups and of methylhydrogenopolysiloxane containing trimethylsiloxy end groups, in the presence of a platinum catalyst.

According to one embodiment variant, the elastomer is a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units.

The organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are especially described in patents EP 242 219, EP 285 886 and EP 765 656 and in patent application JP-A-61-194 009, the content of which is incorporated by way of reference.

According to a preferred embodiment variant, the oily phase of a composition according to the invention contains at least one organopolysiloxane elastomer and more particularly a spherical non-emulsifying organopolysiloxane elastomer.

According to another embodiment variant, the elastomer may also be an emulsifying elastomer.

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

In particular, the organopolysiloxane may be obtained by reaction of polyoxyalkylene (especially polyoxyethylene and/or polyoxypropylene) with dimethylvinylsiloxy end groups and of methylhydrogenopolysiloxane with trimethylsiloxy end groups, in the presence of a platinum catalyst.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are especially described in patents U.S. Pat. Nos. 5,236,986, 5,412,004, 5,837,793 and 5,811,487, the content of which is incorporated by reference.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

The polyglycerolated organopolysiloxane elastomer according to the invention is conveyed in gel form in at least one hydrocarbon-based oil and/or one silicone oil. In these gels, the polyglycerolated elastomer is often in the form of non-spherical particles.

As emerges from the foregoing text, the organopolysiloxane elastomers that are suitable for use in the invention are considered provided that they are capable of gelling the oil or the mixture of oils with which they are combined.

As non-emulsifying elastomers that are suitable for use in the invention, mention may be made especially of those sold under the names KSG-15 and KSG-16 by the company Shin-Etsu.

As polyoxyalkylenated organopolysiloxane elastomers that are suitable for use in the invention, use may be made of those sold under the names KSG-210 and KSG-310 by the company Shin-Etsu.

As polyglycerolated organopolysiloxane elastomers that are suitable for use in the invention, use may be made of those sold under the names KSG-710 and KSG-810 by the company Shin-Etsu.

The lipophilic thickener or gelling agent will generally be present in the composition in a content ranging from 0.1% to 10% by weight, in particular from 0.1% to 4% by weight, especially from 0.2% to 3% by weight and in particular from 0.5% to 4% by weight, relative to the total weight of the said composition.

Preferably, the lipophilic gelling agent will be present in the composition according to the invention in an active material content ranging from 0.1% to 4% by weight, especially from 0.2% to 3% by weight and in particular from 0.5% to 4% by weight, relative to the total weight of the said composition.

According to one particular case, the particulate lipophilic gelling agent may also act as a sebum-pump filler, as is the case for the hydrophobic silica aerogel particles. In this case, a composition of the invention comprising at least hydrophobic silica aerogel particles may or may not also comprise at least one additional sebum-pump filler or at least one additional particulate lipophilic gelling agent.

In particular, a composition of the invention may comprise hydrophobic silica aerogel particles as sole sebum pump and lipophilic gelling agent.

According to another mode, a composition of the invention comprises at least silica microspheres as sebum pump combined with a bentone gel or a hydrophobic silica aerogel.

According to another mode, a composition of the invention comprises at least one hydrophobic silica aerogel as sebum pump combined with a bentone gel.

Hydrophobic Film-Forming Polymer

A composition according to the invention advantageously comprises at least one hydrophobic film-forming polymer.

For the purposes of the invention, the term "polymer" means a compound corresponding to the repetition of one or more units (these units being derived from compounds known as monomers). This or these unit(s) are repeated at least twice and preferably at least 3 times.

For the purposes of the present invention, the term "hydrophobic film-forming polymer" is intended to denote a film-forming polymer that has no affinity for water and, in this respect, does not lend itself to formulation in the form of a solute in an aqueous medium. In particular, the term "hydrophobic polymer" means a polymer having a solubility in water at 25° C. of less than 1% by weight.

The term "film-forming" polymer means a polymer that is capable, by itself or in the presence of an auxiliary film-forming agent, of forming a macroscopically continuous film on a support, especially on keratin materials, and preferably a cohesive film.

In a preferred embodiment, the hydrophobic film-forming polymer is a polymer chosen from the group comprising:

film-forming polymers that are soluble in an organic solvent medium, in particular liposoluble polymers; this means that the polymer is soluble or miscible in the organic medium and forms a single homogeneous phase when it is incorporated into the medium, film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs;

film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizer. These polymer particles are often referred to as "latices"; in this case, the composition must comprise an aqueous phase.

In particular, a composition of the invention may comprise, as hydrophobic film-forming polymer, a polymer chosen from silicone or hydrocarbon-based film-forming polymers, in particular homopolymers and copolymers of a compound bearing an ethylenic unit, acrylic polymers and copolymers, polyurethanes, polyesters, polyureas, cellulose-based polymers such as nitrocellulose, silicone polymers such as silicone resins, silicone polyamides, polymers with a non-silicone organic backbone grafted with monomers containing a polysiloxane, polyamide polymers and copolymers, polyisoprenes, and polyalkene-based (i.e. polyolefin-based) supramolecular polymers, and mixtures thereof.

The said film-forming polymers may be chosen from hydrocarbon-based or silicone film-forming polymers.

Among the hydrocarbon-based film-forming polymers that may be mentioned are:

(meth)acrylic ester homopolymers and copolymers, in particular polymers resulting from the polymerization or copolymerization of methyl, ethyl, propyl, butyl, isobutyl, tert-butyl, pentyl, hexyl, cyclohexyl, 2-ethylhexyl, heptyl, octyl, lauryl, cetyl, stearyl, behenyl, isobornyl or norbornyl acrylate or methacrylate, especially the product sold under the trade name Giovarez AC-5099M by the company Phoenix Chemicals; mention may also be made in this family of block polymers comprising at least a first block and at least a second block, which are mutually incompatible, linked via an intermediate block which comprises at least one constituent monomer of each of the said two blocks. These monomers are of the alkyl, especially methyl, isobutyl or isobornyl, acrylate or methacrylate type or of the (meth)acrylic acid type, such as the poly(isobornyl acrylate/isobornyl methacrylate/isobutyl acrylate/acrylic acid) copolymer whose synthesis is described especially in Example 1 of patent application FR 0 853 223, vinyl ester homopolymers and copolymers, in particular polymers resulting from the polymerization or copolymerization of vinyl acetate, vinyl propionate, vinyl butanoate, vinyl octanoate, vinyl decanoate, vinyl laurate, vinyl stearate, vinyl isostearate, vinyl 2,2-dimethyloctanoate and vinyl dimethylpropionate, vinyl ether homopolymers and copolymers, in particular polymers resulting from the polymerization or copolymerization of ethyl vinyl ether, n-butyl vinyl ether, isobutyl vinyl ether, decyl vinyl ether, dodecyl vinyl ether, cetyl vinyl ether and octadecyl vinyl ether, vinyl amide and (meth)acrylic amide homopolymers and copolymers, cellulose derivatives, especially alkylcelluloses with a linear or branched, saturated or unsaturated $C_1$ to $C_8$ alkyl radical, for instance ethylcellulose and propylcellulose, or cellulose esters such as cellulose acetate, cellulose propionates and cellulose butyrates, polycondensates, in particular polyesters, polyurethanes, polyamides and polyureas, polyalkene-based (i.e. polyolefin-based) supramolecular polymers.

Among the silicone film-forming polymers, mention may be made of:

silicone resins, in particular MQ resins such as trimethyl siloxysilicates, MT resins such as silsesquioxane derivatives, for instance polymethylsilsesquioxanes, polypropylsilsesquioxanes and phenylpropylpolysilsesquioxanes and MQT resins, silicones resulting from the reaction of a silicone resin (MQ) comprising SiOH reactive groups with polyorganosiloxanes also comprising SiOH reactive groups (dimethiconols), especially those present in the product sold under the trade name Bio-PSA 7-4560, silicone gums, which may be polysiloxanes of high molecular mass, of the order of 200 000 to 1 000 000 and greater than 500 000 mPa·s, polyacrylates grafted with linear silicone chains, for instance the silicone-grafted polyalkylmethacrylates present in the product sold under the names KP 545 and 550 by the company Shin-Etsu, polyacrylates grafted with dendrimer silicone chains such as those described in patent application EP 963 751 A2 from Dow Corning and present in the products sold under the names DC FA 4002 ID and DC FA 4001 CM, polyurethane silicones, and silicone polyamides such as those present in the product sold under the trade name DC 2-8179 by the company Dow Corning.

The film-forming polymers defined previously may have a weight-average molecular weight ranging from 2000 to 500 000 and preferably from 4000 to 200 000.

According to a first preferred mode, the film-forming polymer is a silicone film-forming polymer, chosen in particular from silicone resins and acrylate silicones grafted with linear silicone chains or dendrimers.

According to another preferred mode, the film-forming polymer is a hydrocarbon-based film-forming polymer, chosen in particular from block polymers comprising at least a first block and at least a second block, which are mutually incompatible, linked via an intermediate block which comprises at least one monomer of alkyl acrylate or methacrylate type that is a constituent of each of the said two blocks, and polyalkene-based (i.e. polyolefin-based) supramolecular polymers.

Polyalkene-based Supramolecular Polymer

According to a particular mode, the composition of the invention comprises, as hydrocarbon-based film-forming polymer, at least one polyalkene-based (i.e. polyolefin-based) supramolecular polymer, as described in patent application FR 1 002 233.

For the purposes of the present invention, the term "polyalkene-based supramolecular polymer" means a polymer derived from the reaction, especially the condensation, of at least one polyalkene polymer functionalized with at least one reactive group, with at least one junction group functionalized with at least one reactive group capable of reacting with the reactive group(s) of the functionalized polyalkene polymer, said junction group being capable of forming at least three H (hydrogen) bonds and preferably at least four H bonds, preferentially four H bonds.

The terms "polyalkene" and "polyolefin" mean a polymer derived from the polymerization of at least one monomer of alkene type, comprising an ethylenic unsaturation, the said monomer possibly being pendent or in the main chain of the said polymer. The terms "polyalkene" and "polyolefin" are thus directed towards polymers that may or may not comprise a double bond. Preferably, the supramolecular polymers used according to the invention are prepared from a polymer derived from the polymerization of an alkene comprising at least two ethylenic unsaturations.

The supramolecular polymer according to the invention is capable of forming a supramolecular polymer chain or network, by (self)assembly of the said polymer according to the invention with at least one other identical or different polymer according to the invention, each assembly involving at least one pair of paired junction groups, which may be identical or different, borne by each of the polymers according to the invention.

For the purposes of the invention, the term "junction group" means any group comprising groups that donate or accept H bonds, and capable of forming at least three H bonds and preferably at least four H bonds, preferentially four H bonds, with an identical or different partner junction group. These junction groups may be lateral to the polymer backbone (side branching) and/or borne by the ends of the polymer backbone, and/or in the chain forming the polymer backbone. They may be distributed in a random or controlled manner.

Functionalized Polyalkene

The polyalkene polymers are functionalized with at least one reactive group and preferably with at least two reactive groups. The functionalization preferably occurs at the chain ends. They are then referred to as telechelic polymers.

The functionalization groups, or reactive groups, may be attached to the polyalkene polymer via linkers, preferably linear or branched $C_1$-$C_4$ alkylene groups, or directly via a single bond.

Preferably, the functionalized polyalkene polymers have a number-average molecular mass (Mn) of between 1000 and 8000.

Even more preferably, they have a number-average molecular mass of between 1000 and 5000, or even between 1500 and 4500.

Even more preferably, they have a number-average molecular mass of between 2000 and 4000.

Preferably, the functionalized polyalkene polymer, capable of forming all or part of the polymer backbone of the supramolecular polymer according to the invention (preferably, it forms all of the backbone of the polymer), is of formula HO—P—OH in which:

P represents a homo- or copolymer that may be obtained by polymerization of one or more linear, cyclic and/or branched, polyunsaturated (preferably di-unsaturated) $C_2$-$C_{10}$ and preferably $C_2$-$C_4$ alkenes.

P preferably represents a homo- or copolymer that may be obtained by polymerization of one or more linear or branched, $C_2$-$C_4$ diunsaturated alkenes.

More preferably, P represents a polymer chosen from a polybutylene, a polybutadiene (such as a 1,4-polybutadiene or a 1,2-polybutadiene), a polyisoprene, a poly(1,3-pentadiene) and a polyisobutylene, and copolymers thereof.

According to one preferred embodiment, P represents a poly(ethylene/butylene) copolymer.

The preferred poly(ethylene/butylenes) are copolymers of 1-butene and of ethylene. They may be represented schematically by the following sequence of units:

[—CH$_2$—CH$_2$—] and [—CH$_2$CH(CH$_2$—CH$_3$)—]

According to a second preferred embodiment, P is a polybutadiene homopolymer, preferably chosen from a 1,4-polybutadiene or a 1,2-polybutadiene. The polybutadienes may be 1,4-polybutadienes or 1,2-polybutadienes, which may be represented schematically, respectively, by the following sequences of units:

[—CH$_2$—CH=CH—CH$_2$—] (1,4-polybutadienes)

[—CH$_2$—CH(CH=CH$_2$)—] (1,2-polybutadienes)

Preferably, they are 1,2-polybutadienes. Preferably, P is a 1,2-polybutadiene homopolymer.

The functionalized polyalkene polymers may be hydrogenated to avoid the risks of crosslinking. Preferably, the functionalized polyalkene polymers used in the compositions according to the invention are hydrogenated.

Preferably, the polyalkene polymers are hydrogenated and functionalized with at least two OH reactive groups, which are preferably at the ends of the polymers.

Preferably, they have a functionality as hydroxyl end groups of from 1.8 to 3 and preferably in the region of 2.

The polydienes containing hydroxyl end groups are especially defined, for example, in FR 2 782 723. They may be chosen from polybutadiene, polyisoprene and poly(1,3-pentadiene) homopolymers and copolymers. Mention will be made in particular of the hydroxylated polybutadienes sold by the company Sartomer, for instance the Krasol® Resins and the Poly Bd® Resins. Preferably, they are hydrogenated dihydroxylated 1,2-polybutadiene homopolymers, such as the range Nisso-PB I, GI3000, GI2000 and GI1000 sold by the company Nisso, which may be represented schematically by the following formula:

Preferably, n is between 14 and 105 and preferably between 20 and 85.

Junction Group

The supramolecular polymers according to the invention also have in their structure at least one residue of a junction group capable of forming at least three H bonds and preferably at least four H bonds, the said junction group being initially functionalized with at least one reactive group.

Unless otherwise mentioned, the term "junction group" means in the present description the group without its reactive function.

The reactive groups are attached to the junction group via linkers L.

Preferably, the linker is chosen from the groups:
 C$_5$-C$_{20}$ (alkyl)cycloalkylene alkylene, such as isophorone,
 C$_{11}$-C$_{25}$ alkylene-biscycloalkylene, such as 4,4'-methylene biscyclohexylene,
 C$_1$-C$_{20}$ alkylene such as —(CH$_2$)$_2$—; —(CH$_2$)$_6$—; —CH$_2$CH(CH$_3$)—CH$_2$—C(CH$_3$)$_2$—CH$_2$—CH$_2$, and
 C$_6$-C$_{20}$ (alkyl) phenylene, such as 2-methyl-1,3-phenylene.

Preferably, L is chosen from: -isophorone-; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylene biscyclohexylene; 2-methyl-1,3-phenylene.

According to one particularly preferred embodiment, the linker is an alkylcycloalkylene alkylene.

Preferably, according to this embodiment, the linker is an isophorone group. The term "isophorone" means the following group:

The said reactive groups functionalizing the junction group must be capable of reacting with the —OH reactive group(s) borne by the functionalized polyalkene.

Reactive groups that may be mentioned include isocyanate (—N=C=O) and thioisocyanate (—N=C=S) groups. Preferably, it is a group —N=C=O (isocyanate).

The functionalized junction groups capable of forming at least three H bonds may comprise at least three identical or different functional groups, and preferably at least four functional groups, chosen from:

$$\diagdown C=O \quad \diagdown C=N— \quad —\underset{|}{N}H$$

These functional groups may be classified into two categories:
functional groups that donate H bonds:

$$—\underset{|}{N}H$$

functional groups that accept H bonds:

$$\diagdown C=O \quad \diagdown C=N—$$

According to one preferred embodiment, the junction groups are chosen from 2-ureidopyrimidone and 6-methyl-2-ureidopyrimidone.

Preferably, the preferred junction group is 6-methyl-2-ureidopyrimidone.

In particular, the functionalized junction groups capable of reacting with the functionalized polyalkene polymer to give the supramolecular polymer according to the invention are preferably of formula:

in which L is as defined above.

According to one particularly preferred embodiment, the junction group is of formula

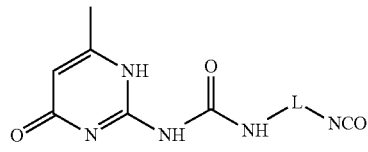

in which L is isophorone.

In one particularly preferred embodiment, the supramolecular polymer of the invention corresponds to the formula:

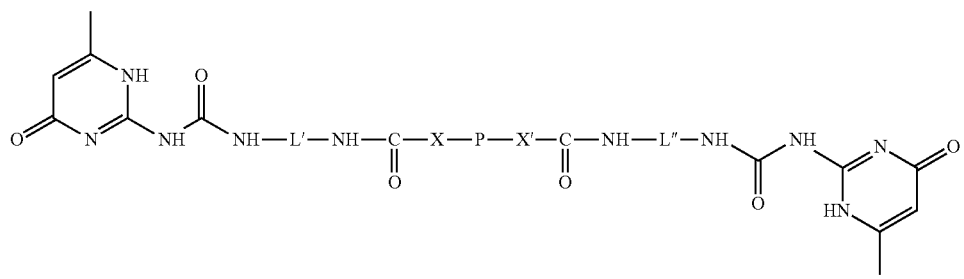

in which:

L' and L" have, independently of each other, the meaning given above for L;

X, X'=O and P has the meaning given above for the functionalized polyalkene polymer.

Preferably, L' and L" represent a saturated or unsaturated divalent $C_1$-$C_{20}$ carbon-based group chosen in particular from a linear or branched $C_1$-$C_{20}$ alkylene; a $C_5$-$C_{20}$ (alkyl) cycloalkylene, an alkylene-biscycloalkylene, a $C_6$-$C_{20}$ (alkyl)arylene. Preferably, L' and L" represent a group from among: -isophorone-; —$(CH_2)_2$—; —$(CH_2)_6$—; —$CH_2CH(CH_3)$—$CH_2$—$C(CH_3)_2$—$CH_2$—$CH_2$; 4,4'-methylene bis-cyclohexylene; 2-methyl-1,3-phenylene.

Preferably, L' and L" are identical.

Preferably, L' and L" are an isophorone group.

Preferably, P is hydrogenated and represents a polyethylene, a polybutylene, a polybutadiene, a polyisoprene, a poly(1,3-pentadiene), a polyisobutylene, or a copolymer thereof, especially a poly(ethylene/butylene).

Preferably, P is a hydrogenated polybutadiene, preferably a hydrogenated 1,2-polybutadiene.

In one particularly preferred embodiment, the supramolecular polymer of the invention corresponds to the formula:

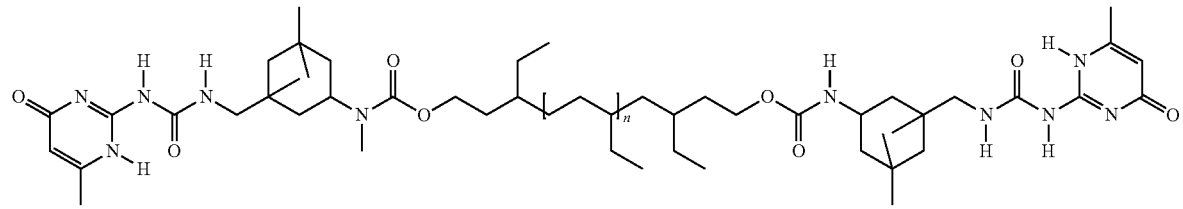

In particular, a composition of the invention comprises, as hydrophobic film-forming polymer, at least one supramolecular polymer of formula

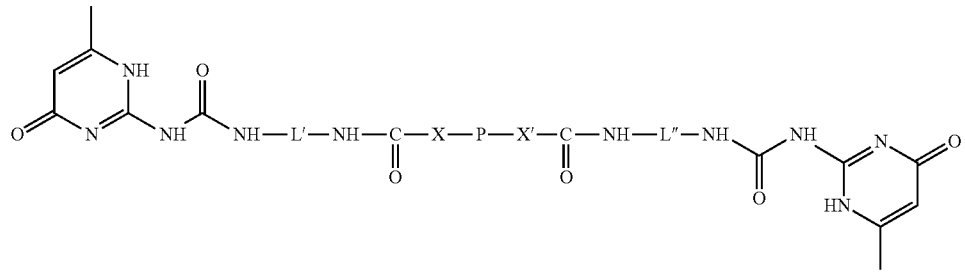

in which:

L' and L" are, independently of each other, a group from among: -isophorone-; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylene biscyclohexylene; 2-methyl-1,3-phenylene, preferably an isophorone group, —X, X'=O and P is hydrogenated and represents a polyethylene, a polybutylene, a polybutadiene, a polyisoprene, a poly(1,3-pentadiene), a polyisobutylene, or a copolymer thereof, especially a poly(ethylene/butylene), and is preferably a hydrogenated polybutadiene, more preferably a hydrogenated 1,2-polybutadiene.

According to another particular mode, a composition of the invention comprises as hydrophobic film-forming polymer at least one vinyl polymer bearing at least one carbosiloxane dendrimer-based unit, as described in patent application FR 0 957 629.

A cosmetic skin makeup composition according to the invention may comprise from 0.1% to 20% by weight of active material, preferably from 0.2% to 15% by weight and even more preferentially from 0.5% to 10% by weight of hydrophobic film-forming polymer(s).

Additional Fillers

Needless to say, a makeup composition according to the invention may comprise, besides a sebum-pump filler as defined previously, one or more additional filler(s), i.e. not in accordance with the oil uptake requirement as defined previously.

According to a first embodiment, the composition is free of additional filler.

According to a second embodiment, the composition comprises at least one additional filler. According to this embodiment, such fillers may be present in a proportion of from 0.01% to 35% by weight and preferably 0.1% to 20% by weight relative to the total weight of the composition. Preferably, a composition according to the invention, when it is in the form of a foundation, comprises at least one additional filler.

Illustrations of these additional fillers that may be mentioned include talc, mica, silica, kaolin, calcium carbonate, barium sulfate, nylon (especially Orgasol) powder and polyethylene powder, Teflon, starch, boron nitride, copolymer microspheres such as Expancel (Nobel Industrie) and silicone resin microbeads (for example Tospearls from Toshiba); silicone fillers; and also mixtures thereof.

A cosmetic makeup composition according to the invention also comprises a cosmetically acceptable medium that may comprise the usual ingredients, as a function of the intended use of the composition.

Dyestuff(s)

A composition for making up the skin according to the invention comprises at least one dyestuff, in particular at least one pulverulent dyestuff. The dyestuff according to the invention are distinct from fillers. The dyestuff is especially chosen from organic or mineral dyestuffs, especially such as the pigments or nacres conventionally used in cosmetic compositions, liposoluble or water-soluble dyes, materials with a specific optical effect, and mixtures thereof.

The pulverulent dyestuffs are in particular chosen from organic or mineral pulverulent dyestuffs, especially of pigment or nacre type, materials with a specific optical effect, and mixtures thereof.

In particular, the pulverulent dyestuffs are chosen from pigments and nacres, and mixtures thereof.

Pigments

The term "pigments" should be understood to mean white or coloured, mineral or organic particles which are insoluble in an aqueous solution and are intended for colouring and/or opacifying the resulting film.

As mineral pigments that may be used in the invention, mention may be made of titanium oxides, zirconium oxides or cerium oxides, and also zinc oxides, iron oxides or chromium oxides, ferric blue, manganese violet, ultramarine blue and chromium hydrate. Iron oxide or titanium dioxide pigments are preferably used.

In particular, a composition of the invention comprises, as pulverulent dyestuffs, at least mineral pigments chosen from titanium oxides and iron oxides, and mixtures thereof.

The pigment may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The dyestuff may also comprise a pigment having a structure which may be, for example, of the type such as silica microspheres containing iron oxide. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPPs) described in documents EP-A-542 669, EP-A-787 730, EP-A-787 731 and WO-A-96/08537.

Nacres

The term "nacres" should be understood as meaning iridescent or non-iridescent coloured particles of any form, especially produced by certain molluscs in their shell or alternatively synthesized, which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Materials with an Optical Effect

The cosmetic composition according to the invention may also contain at least one material with a specific optical effect.

This effect is different from a simple conventional tint effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic glint, goniochromic colouring agents, diffracting pigments, thermochromic agents, optical brighteners, and also fibres, in particular interference fibres. Needless to say, these various materials may be combined so as to afford the simultaneous manifestation of two effects, or even of a novel effect in accordance with the invention.

The particles with a metallic glint that may be used in the invention are chosen in particular from:
- particles of at least one metal and/or of at least one metal derivative,
- particles comprising a single-material or multi-material organic or mineral substrate, at least partially coated with at least one layer with a metallic glint comprising at least one metal and/or at least one metal derivative, and
- mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" denotes compounds derived from metals, in particular oxides, fluorides, chlorides and sulfides.

The goniochromatic colouring agent may be chosen, for example, from multilayer interference structures and liquid-crystal colouring agents.

The dyestuff(s) may or may not be totally or partially surface-treated, with at least one lipophilic or hydrophobic treating agent. The said agent may be chosen especially from silicones, fatty acids, for instance stearic acid; metal soaps, for instance aluminium dimyristate, the aluminium salt of hydrogenated tallow glutamate; perfluoroalkyl phosphates, polyhexafluoropropylene oxides; perfluoropolyethers; amino acids; N-acylamino acids or salts thereof; lecithin, isopropyl triisostearyl titanate, isostearyl sebacate, and mixtures thereof.

Preferably, the amount of dyestuffs in a composition according to the invention is between 0.01% and 40% by weight and especially between 0.1% and 30% by weight, or even between 1% and 20% by weight, relative to the total weight of the composition. In particular, the pulverulent dyestuffs in a foundation product will be present in a content ranging from 8% to 30% by weight and preferably from 12% to 25% by weight relative to the total weight of the said composition.

In particular, a composition of the invention will comprise as pulverulent dyestuffs mineral pigments, and preferably titanium oxides and iron oxides, especially representing from 8% to 30% by weight and preferably from 12% to 25% by weight relative to the total weight of the said composition.

According to a particular mode, the pigments are not coated.

According to another particular mode, the pigments are coated.

Continuous Oil Phase

A composition of the invention comprises at least one continuous liquid fatty phase, especially at least one oil as mentioned below.

The term "oil" means any fatty substance that is in liquid form at room temperature (20-25° C.) and at atmospheric pressure.

The oil phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They may be of animal, plant, mineral or synthetic origin.

The term "non-volatile oil" means an oil that remains on the skin or the keratin fibre at room temperature and atmospheric pressure. More specifically, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing the said oil or the said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of surface area (cm$^2$) and per unit of time (minutes).

The term "volatile oil" means any non-aqueous medium that is capable of evaporating from the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

For the purposes of the present invention, the term "silicone oil" means an oil comprising at least one silicon atom, and especially at least one Si—O group.

The term "fluorinated oil" is understood to mean an oil comprising at least one fluorine atom.

The term "hydrocarbon-based oil" is understood to mean an oil comprising mainly hydrogen and carbon atoms.

The liquid fatty phase of the composition according to the invention comprises at least volatile oils chosen from slow volatile oils and/or fast volatile oils.

Fast Volatile Oils

The composition according to the invention advantageously comprises at least one fast volatile oil.

For the purposes of the present invention, the term "fast volatile oil" means an oil chosen from the volatile oils as defined previously, having an evaporation rate of greater than or equal to 0.05 mg/cm$^2$/min, in particular ranging from 0.05 to 200 mg/cm$^2$/min, especially greater than or equal to 0.054 mg/cm$^2$/min, in particular ranging from 0.054 to 100 mg/cm$^2$/min and preferentially ranging from 0.054 to 30 mg/cm$^2$/min.

In particular, a composition of the invention comprises, in its oil phase, at least one fast volatile oil with an evaporation rate of between 0.5 mg/cm$^2$/min and 200 mg/cm$^2$/min.

The volatile hydrocarbon-based oils may be chosen from hydrocarbon-based oils containing from 8 to 16 carbon atoms, and especially branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, and, for example, the oils sold under the trade names Isopar® or Permethyl®.

Volatile oils that may also be used include volatile silicones, for instance volatile linear or cyclic silicone oils, especially those with a viscosity ≤5 centistokes (5×10$^{-6}$ m$^2$/s), and especially containing from 2 to 10 silicon atoms and preferably from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

In particular, the composition of the invention comprises hydrocarbon-based volatile oils, preferably isododecane, and/or linear silicone volatile oils.

According to a particular embodiment, the content of fast volatile solvents (fast volatile oil and fast volatile solvents present in the aqueous phase, such as water and C2-C5 monoalcohols) is greater than 60% by weight and preferably greater than or equal to 65% by weight relative to the total weight of the composition.

Slow Volatile Oils

The composition according to the invention advantageously also comprises at least one slow volatile oil.

For the purposes of the present invention, the term "slow volatile oil" means an oil chosen from the volatile oils as defined previously, having an evaporation rate of between 0.01 and 0.05 mg/cm$^2$/min.

In particular, a cosmetic composition of the invention also comprises, in its oil phase, at least one slow volatile oil with an evaporation rate of between 0.01 mg/cm$^2$/min and 0.05 mg/cm$^2$/min.

In particular, the slow volatile oil(s) may be chosen from isohexadecane, cyclohexasiloxane, diethyldodecane (for example Cetiol DD from the company Cognis) and hexyl trimethicone, and mixtures thereof.

Preferably, the composition will comprise, as slow volatile oil, at least isohexadecane.

The volatile oils (slow volatile oils and fast volatile oils) may be present in the composition in a content ranging from 15% to 75% by weight relative to the total weight of the composition, preferably ranging from 20% to 70% by weight and more preferentially ranging from 22% to 65% by weight relative to the total weight of the composition.

Additional Oils

The composition may also comprise at least one additional oil, chosen in particular from dry oils and other non-volatile oils, preferably in a content of less than or equal to 10% by weight and in particular less than or equal to 5% by weight relative to the total weight of the said composition.

The composition according to the invention may comprise at least one dry oil.

For the purposes of the present patent application, the term "dry oil" means an oil chosen from oils with a viscosity of less than or equal to 0.01 Pa·s (10 cPs), especially ranging from 0.003 to 0.01 Pa·s, a surface tension of between 21 and 31 mN/m and an evaporation rate of less than 0.002 mg/cm$^2$/min.

The preferred dry oils are aprotic oils containing from 12 to 22 carbon atoms, preferably from 14 to 22 carbon atoms and more preferentially from 16 to 20 carbon atoms.

The term "aprotic oil" means an oil comprising few or no hydrogen atoms bonded to a highly electronegative atom such as O or N.

In particular, the term "aprotic oil" means oils which may comprise, as a function of the yield of their synthesis, residual groups bearing a labile hydrogen atom (for example residual OH, NH and/or COOH groups) in a numerical content of less than or equal to 5%.

Among the oils corresponding to this definition, mention may be made of:

ester oils such as isopropyl myristate, isopropyl palmitate, 2-ethylhexyl benzoate, isodecyl neopentanoate, 2-ethylhexyl 2-ethylhexanoate and isononyl isononanoate, ether oils such as dicaprylyl ether and dicaprylyl carbonate (Cetiol CC), carbonate oils such as di-2-ethylhexyl carbonate, and mixtures thereof.

According to a preferred embodiment, the dry oil is isononyl isononanoate.

Besides the dry oil(s) defined previously, the non-volatile fraction of the liquid fatty phase may comprise at least one additional non-volatile oil.

According to one particular embodiment, the non-volatile oil is chosen from oils with an evaporation rate of less than 0.002 mg/cm$^2$/min.

The additional non-volatile oils may be chosen especially from non-volatile hydrocarbon-based oils, where appropriate fluorinated, and/or non-volatile silicone oils.

Non-volatile hydrocarbon-based oils that may in particular be mentioned include:

hydrocarbon-based oils of animal origin, hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms, other than those corresponding to the definition of dry oils, such as diisocetyl ether, linear or branched hydrocarbons of mineral or synthetic origin, such as petroleum jelly, polydecenes, hydrogenated polyisobutene such as Parleam®, squalane and liquid paraffins, and mixtures thereof;

synthetic esters, other than those corresponding to the definition of the dry oils, such as oils of formula $R_1COOR_2$ in which $R_1$ represents a linear or branched fatty acid residue containing from 1 to 40 carbon atoms and $R_2$ represents an especially branched hydrocarbon-based chain containing from 1 to 40 carbon atoms, on condition that $R_1+R_2 \geq 10$, for instance purcellin oil (cetostearyl octanoate), $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalcohol heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol;

higher fatty acids such as oleic acid, linoleic acid or linolenic acid, and mixtures thereof. The non-volatile silicone oils that may be used in the composition according to the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

According to a particular mode, a composition of the invention also comprises at least one non-volatile solvent, in particular a non-volatile oil, a polyol and/or a surfactant, in a content of less than or equal to 15% by weight and in particular less than or equal to 10% by weight relative to the total weight of the said composition.

Preferably, a composition of the invention is characterized in that the content of fast volatile oil(s)> content of slow volatile oil(s)> content of non-volatile oil(s).

Aqueous Phase

A composition according to the invention may also comprise an aqueous phase, which may represent 0% to 40% by weight relative to the total weight of the composition.

This aqueous phase may be formed essentially from water, or may comprise a mixture of water and of water-miscible solvent (miscibility in water of greater than 50% by weight at 25° C.) chosen especially from monoalcohols containing 1 to 5 carbon atoms such as ethanol, isopropanol, glycols containing 2 to 8 carbon atoms such as propylene glycol, ethylene glycol, 1,3-butylene glycol, dipropylene glycol, $C_3$-$C_4$ ketones and $C_2$-$C_4$ aldehydes, and mixtures thereof.

According to a particular mode, the composition of the invention comprises at least monoalcohols containing 1 to 5 carbon atoms such as ethanol and isopropanol, and optionally water for the W/O emulsion forms.

Additive(s)

A makeup and/or care composition according to the invention may also comprise at least one agent usually used in cosmetics, chosen, for example, from reducing agents, thickeners, surfactants, film-forming agents that are especially hydrophobic, silicone elastomers, softeners, antifoams, moisturizers, UV-screening agents, ceramides; cosmetic active agents; peptizers, fragrances, proteins, vitamins, propellants, hydrophilic or lipophilic, film-forming or non-film-forming polymers; lipophilic or hydrophilic gelling agents. The above additives are generally present in an amount for each of them of between 0.01% and 10% by weight relative to the total weight of the composition. Needless to say, a person skilled in the art will take care to select the constituents of the composition such that the advantageous properties associated with the invention are not, or are not substantially, adversely affected.

A makeup and/or care composition according to the invention may especially be in the form of an oily suspension, an oily dispersion, an oily solution, a gel, a water-in-oil emulsion (W/O) or a multiple emulsion (O/W/O), or in the form of a cream, a mousse, a stick, a dispersion of vesicles, especially of ionic or nonionic lipids, a two-phase or multi-phase lotion, a spray, a powder or a paste.

According to a particular mode, the composition of the invention is a water-in-oil emulsion.

According to another particular mode of the invention, the compositions according to the invention are anhydrous or contain less than 3% by weight of water and preferably less than 1% by weight of water relative to the total weight of the composition. The term "anhydrous" especially means that water is preferably not deliberately added to the composition, but may be present in trace amount in the various compounds used in the composition.

A person skilled in the art can choose the appropriate formulation form, and also its method of preparation, on the basis of his general knowledge, taking into account first the nature of the constituents used, in particular their solubility in the support, and secondly the application envisaged for the composition.

In the description and in the examples that follow, unless otherwise mentioned, the percentages are weight percentages.

The examples below are given as non-limiting illustrations of the field of the invention.

EXAMPLES

Effect of the Particulate Gelling Agent on the Properties of Mattness and Remanence of the Mattness/Colour with Respect to Sebum and/or Sweat Water-in-Oil Foundation

| | Chemical name | F1 Control without lipophilic gelling agent | F2 | F3 |
|---|---|---|---|---|
| B1 | Magnesium sulfate 7 H2O | 0.7 | 0.7 | 0.7 |
| A4 | Silica microspheres (Sunsphere H-33 Solesphere H-33 from AGC SI-TECH) | 1 | 1 | 1 |
| D | Trimethylated silica (free-flowing powder) (VM-2270 Aerogel Fine Particles from Dow Corning) | — | 0.5 | 2 |
| A4 | Perlite (25 microns) Optimat 1430 OR by the company World Minerals | 0.2 | 0.2 | 0.2 |
| A3 | Anatase titanium oxide coated with aluminium stearoyl glutamate (97/3) (CI: 77891) | 8.98 | 8.98 | 8.98 |
| A3 | Iron oxides coated with aluminium stearoyl glutamate | 3.02 | 3.02 | 3.02 |
| A1 | Isohexadecane | 1.6 | 1.6 | 1.6 |
| A1 | Stabilized (0.1% BHT) 2-ethylhexyl 4-p-methoxycinnamate | 3 | 3 | 3 |
| A4 | Nylon 12 powder | 3 | 2.5 | 1 |
| A1 | Cyclohexadimethylsiloxane (viscosity: 8 cSt) | 15.7 | 15.7 | 15.7 |
| A1 | Oxyethylenated polydimethylsiloxane (DP: 70 - viscosity: 500 cSt) | 3 | 3 | 3 |
| A2 | Butyl acrylate copolymer containing dendritic silicone side chains: [tri(trimethylsiloxy)siloxy-ethyldimethylsiloxy]silylpropyl methacrylate in isododecane: 40/60 (Dow Corning FA 4002 ID Silicone Acrylate) | 10 | 10 | 10 |
| B1 | 1,3-Butylene glycol | 6 | 6 | 6 |
| C | Denatured 96° ethyl alcohol | 8 | 8 | 8 |
| B1 | Microbiologically clean deionized water | qs 100 | qs 100 | qs 100 |
| A1 | Isododecane | 1 | 1 | 1 |

Manufacturing Procedure:

The constituents of phase A1 were weighed out in the main beaker and were stirred with a Moritz blender until homogenized, while maintaining at room temperature.

Next, phase A2 was added at room temperature, by stirring using a Moritz blender until homogenized.

Phase A3 is prepared separately by milling three times in a three-roll mill the mixture of pigments and of cyclohexasiloxane.

This phase A3 is then added, with continued stirring, along with phase A4.

The aqueous phase B is also prepared separately, by weighing out in a beaker the butylene glycol and the magnesium sulfate, and by adding water preheated to 95° C.

The aqueous phase is stirred using a magnetic bar until homogenized.

The emulsion is formed at room temperature by pouring the aqueous phase B into the fatty phase and stirring with a Moritz blender until homogenized.

Phase C (ethanol) is finally added.

The product obtained is stirred using a Rayneri blender (paddles) for 10 minutes between 50 and 60 rpm.

Compositions F1, F2 and F3 have, respectively, viscosities of 0.65, 0.78 and 4 Pa·s using a viscometer with a No. 3 spindle at 25° C.

Anhydrous Foundation
Synthesis of a Supramolecular Polymer: Synthesis of the Ureidopyrimidone Difunctionalized Polymer GI2000

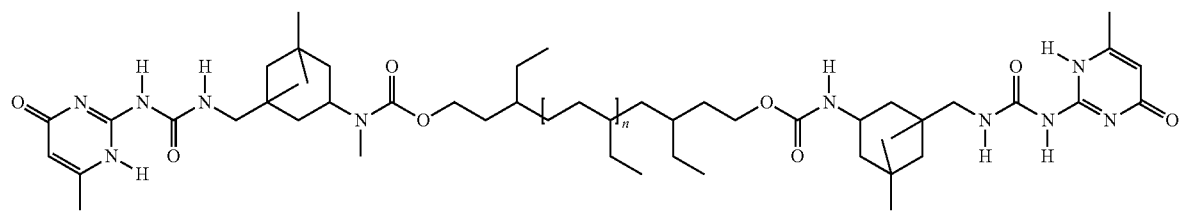

106.1 g of dihydroxylated hydrogenated 1,2-polybutadiene polymer (GI2000 from Nisso, Mn=3300 measured by GPC according to the protocol described previously) are heated in the presence of 22 mg of catalyst (dibutyltin dilaurate) at 80° C., under reduced pressure, for two hours. The temperature of the mixture is reduced to 20° C., under argon, followed by addition of 10 ml of isododecane and 19.3 g of isophorone diisocyanate (IPDI). The mixture is stirred for 16 hours at 20° C. under a controlled atmosphere, and is then heated to 120° C., followed by addition of 25 ml of propylene carbonate. 12 g of 6-methylisocytosine are added, resulting in a homogeneous white suspension. This suspension is heated to 140° C. and stirred at this temperature for 6 hours. The reaction is monitored by infrared spectroscopy, up to the total disappearance of the characteristic peak for isocyanates (2250 cm$^{-1}$). The mixture is then reduced again to 30° C., and 400 ml of heptane, 200 ml of THF and 50 ml of ethanol are added, followed by filtration through Celite. The mixture is then stripped with isododecane.

A solution of the polymer in isododecane, with 25% by weight of polymer, is finally obtained; the polymer is characterized by GPC (Mn=7000 and polydispersity index=2.05).

The polymer solution is used to prepare the following anhydrous foundation:

| | Chemical name | F4 | F5 | F6 | F7 Control without lipophilic gelling agent |
|---|---|---|---|---|---|
| A | Amorphous silica microspheres (particle size: 3 microns) (Sunsphere H-33 Solesphere H-33 from AGC SI-TECH) | 4 | 4 | 4 | 4 |
| B | Smectite: Modified magnesium silicate at 10% in isododecane (Bentone Gel ISD V from Elementis) | 30 | 30 | — | — |
| C | Trimethylated silica (free-flowing powder) (VM-2270 Aerogel Fine Particles from Dow Corning) | — | 0.5 | 3 | — |
| B | Titanium oxide (untreated anatase) (CI: 77891) | 9.98 | 9.98 | 9.98 | 9.98 |

-continued

| | Chemical name | F4 | F5 | F6 | F7 Control without lipophilic gelling agent |
|---|---|---|---|---|---|
| B | Iron oxides | 2.02 | 2.02 | 2.02 | 2.02 |
| | Isohexadecane | 4.5 | 4.0 | 4.5 | 4.5 |
| A | Solution of ureidopyrimidone difunctionalized supramolecular polymer GI2000 at 25% in isododecane, as prepared above | 33 | 33 | 33 | 33 |
| A | Cyclo-hexadimethylsiloxane (viscosity: 8 cSt)(Xiameter PMX-0246 Cyclo-hexasiloxane from Dow Corning) | 6.5 | 6.5 | 6.5 | 6.5 |
| A | Caprylyl methicone (PZ-3196 from Dow Corning) | 5 | 5 | 5 | 5 |
| A | Denatured 96° ethyl alcohol | 4 | 4 | 4 | 4 |
| B | Isododecane | 1 | 1 | 28 | 31 |
| | TOTAL | 100 | 100 | 100 | 100 |

Manufacturing Procedure:
The raw materials of phase A were weighed out in the main beaker;
The pigments were ground in part of the bentone gel, supramolecular polymer solution and isododecane;
Phase B was added to A with stirring (vortex) without heating;

Phase C was added and the mixture was homogenized until fully dispersed.

Compositions F4 and F5 have, respectively, viscosities of 3.04 and 3.87 Pa·s using a viscometer with a No. 3 spindle at 25° C.

Evaluation of the Mattness and Remanence Properties in the Presence of Sebum and/or Sweat The W/O foundation formulations (F1, F2 and F3) and the anhydrous formulations (F4, F5 and F7) were evaluated on models with greasy skin, according to the following protocols:

standard protocol at room T° C.: evaluation of the mattness, homogeneity and colour after application of 100 mg of composition to half a face with evaluation times at T0, Timm, T 3 hours: evaluation of the resistance to sebum protocol under hot/humid conditions at 37° C. and 60% humidity: evaluation of the mattness, homogeneity and colour after application of 100 mg of composition to half a face with evaluation times at T0, Timm, T 30 minutes: evaluation of the resistance to sweat Protocol for the Instrumental Measurements of the Immediate Colour and the Colour Remanence A colorimetric measurement of the skin before and after making up is performed by measuring the red, yellow and luminance indices, a*, b* and L*, respectively. For each woman, an image is acquired using a Chromasphere, at a definition of 410×410 pixels.

The results are expressed in the following manner: The colour is quantified by the red, yellow and luminance indices analysed by the camera (a*, b* and L*, respectively). The colour remanence is calculated by the variation of these variables after 3 hours of makeup (deltaE94).

More specifically, the measurements are performed on a panel of individuals, who are kept in an air-conditioned waiting room (22° C.±2° C.) 15 minutes before the start of the test. They remove their makeup and an image of one of their cheeks is acquired using a Chromasphere at a definition of 410×410 pixels. This image allows measurement of the colour at T0 before applying makeup. Next, about 100 mg of the cosmetic composition are weighed out on a watch glass, and are applied with the bare fingers onto the half-face on which the measurement at T0 was taken.

After a drying time of 15 minutes, an image of the made-up cheek is acquired using a Chromasphere. This image allows measurement of the colour just after applying makeup (Timm). The models then return to an air-conditioned room for 3 hours (30 minutes in the case of the protocol under hot/humid conditions). Finally, an image of the made-up cheek after waiting for 3 hours (or 30 minutes) is acquired using the Chromasphere. This image allows measurement of the colour after 3 hours of makeup (T3 h) or T30 min.

The results are expressed by calculating the difference (Timm−T0), which measures the effect of the makeup. The difference (T3 h−Timm or T30 min−Timm) measuring the remanence of this effect is then calculated. Each image obtained using the camera is processed in colour. The colour is quantified by the red and yellow indices, the luminance and the colour difference (respectively, a*, b*L and deltaE). The delta E, dE or ΔE, is defined as a measurement of the difference between two colours.

Here is the formula established in 1976:

$$|\Delta E^*| = \sqrt{|(L_1-L_2)^2 + (a_1-a_2)^2 + (b_1-b_2)^2|}$$

where:

$L_1$, $a_1$, $b_1$ are the coordinates in the colorimetric space of the first colour to be compared and $L_2$, $a_2$, $b_2$ are those of the second colour.

Protocol for the Instrumental Measurements of the Immediate Mattness and the Mattness Remanence The mattness effect and mattness remanence of the application of the W/O emulsion described previously are evaluated on the skin of a panel of individuals. The mattness and the mattness remanence may be measured by means of the protocol described below. The mattness of a region of skin, for example facial skin, is measured using a polarimetric camera, which is a black and white polarimetric imaging system, with which images are acquired in parallel (P) and crossed (C) polarized light. By analysing the image resulting from subtraction of the two images (P—C), the gloss is quantified, by measuring the average greyscale of the glossiest 5% of pixels corresponding to the glossy areas.

More specifically, the measurements are performed on a panel of individuals, who are kept in an air-conditioned waiting room (22° C.±2° C.) 15 minutes before the start of the test. They remove their makeup and an image of one of their cheeks is acquired using the polarimetric camera. This image allows measurement of the gloss at T0 before applying makeup. Next, about 100 mg of the composition described above are weighed out in a watch glass, and are applied with the bare fingers onto the half-face on which the measurement at T0 was taken. After a drying time of 15 minutes, an image of the made-up cheek is acquired using the polarimetric camera. This image allows measurement of the gloss just after applying makeup (Timm). The models then return to an air-conditioned room for 3 hours (30 minutes in the case of the protocol under hot/humid conditions). Finally, an image of the made-up cheek after waiting for 3 hours is acquired using the polarimetric camera. This image allows measurement of the gloss after 3 hours of makeup (T3 h) or 30 minutes (T30 min). The results are expressed by calculating the difference (Timm−T0), which measures the effect of the makeup. A negative value means that the makeup reduces the gloss of the skin and that it thus has a matt effect.

The difference (T3 h−Timm) or (T30 min−Timm) measuring the remanence of this effect is then calculated. The value obtained should be as low as possible, which means that the mattness of the makeup does not change over time.

Summary of the Instrumental Results:

Standard 3-Hour Remanence Results: Remanence with Respect to Sebum

+ mild effect or low remanence

++ moderate effect or moderate remanence

+++ strong effect or good remanence

++++ very strong effect or very good remanence

|  | F1<br>Control without<br>particulate<br>lipophilic<br>gelling agent<br>W/O | F2<br>0.5%<br>Aerogel<br>W/O | F3<br>2%<br>Aerogel<br>W/O | F7<br>Control without<br>particulate<br>lipophilic<br>gelling agent<br>Anhydrous | F4<br>3%<br>bentone<br>Anhydrous | F5<br>3%<br>bentone +<br>0.5%<br>Aerogel<br>Anhydrous |
|---|---|---|---|---|---|---|
| Initial mattness | ++ | +++ | +++ | +++ | +++ | ++++ |
| Remanence of the mattness after 3 hours | ++++ | ++++ | ++++ | + | +++ | +++ |
| Colour remanence | +++ | +++ | ++++ | ++ | +++ | ++++ |

The presence of smectite particles (bentone) in an anhydrous composition also comprising a sebum pump, highly improves the mattness remanence. The presence of aerogel particles in a W/O composition also comprising a sebum pump, or in an anhydrous composition also comprising a sebum pump and optionally an additional particulate lipophilic gelling agent (smectite), improves the initial mattness and the colour remanence. The mattness remanence is, itself, conserved.

The compositions according to the invention thus show good resistance to sebum.

30-Minute Extreme Remanence Results: Remanence with Respect to Sweat

|  | F1<br>Control without<br>particulate<br>lipophilic<br>gelling agent<br>W/O | F2<br>0.5%<br>Aerogel<br>W/O | F3<br>2%<br>Aerogel<br>W/O | F7<br>Control without<br>particulate<br>lipophilic<br>gelling agent<br>Anhydrous | F4<br>3%<br>bentone<br>Anhydrous | F5<br>3%<br>bentone +<br>0.5%<br>Aerogel<br>Anhydrous |
|---|---|---|---|---|---|---|
| Initial mattness | + | ++ | +++ | +++ | +++ | ++++ |
| Remanence of the mattness after 30 minutes | +++ | +++ | ++++ | + | +++ | +++ |
| Colour remanence | ++ | +++ | ++++ | ++ | +++ | +++ |

In the case of the protocol under hot/humid conditions, an improvement in the initial mattness and good remanence of the colour and the mattness were observed. The compositions according to the invention thus show good resistance to sweat.

As a result, they are makeup products that are particularly intended for greasy skin and for people subject to hot and/or humid atmospheric conditions.

The invention claimed is:
1. A fluid cosmetic skin makeup composition, comprising, in a physiologically acceptable medium:
 a continuous oil phase;
 a sebum-pump filler with an oil uptake greater than or equal to 1 ml/g and a pulverulent dyestuff, wherein the sebum pump is at least one selected from the group consisting of a silica, a silica silylate, an acrylic polymer powder, a perlite, a magnesium carbonate, and a silicone filler;
 a hydrophobic film-forming polymer, and;
 a lipophilic gelling agent selected from the group consisting of an organomodified clay, a hydrophobic fumed silica, a hydrophobic silica aerogel, and a combination thereof;
 wherein the composition comprises a solids content of greater than or equal to 15%;
 wherein the hydrophobic film-forming polymer of formula

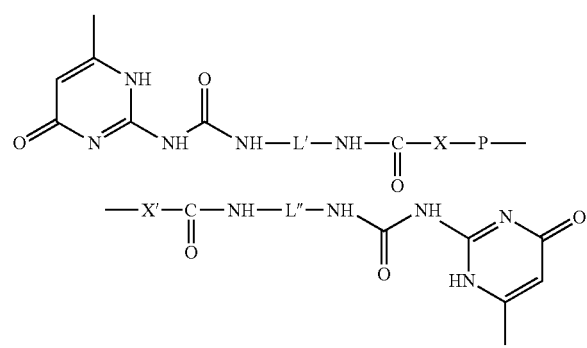

in which:

L' and L" are independently selected from a group consisting of -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylene biscyclohexylene, 2-methyl-1,3-phenylene;

X, X'=O;

P is hydrogenated and is selected from a group consisting of a polyethylene, a polybutylene, a polybutadiene, a polyisoprene, a poly(1,3-pentadiene), a polyisobutylene, or a copolymer thereof.

2. The cosmetic composition according to claim 1, which has a viscosity, at 25° C. and at a shear rate of 200 min$^{-1}$, ranging from 0.5 to 5 Pa·s.

3. The cosmetic composition according to claim 1, wherein the continuous oil phase comprises a fast volatile oil with an evaporation rate between 0.5 mg/cm$^2$/min and 200 mg/cm$^2$/min.

4. The cosmetic composition according to claim 1, wherein the continuous oil phase comprises a slow volatile oil with an evaporation rate between 0.01 mg/cm$^2$/min and 0.05 mg/cm$^2$/min.

5. The cosmetic composition according to claim 1, further comprising at least one selected from the group consisting of a non-volatile solvent, a polyol and a surfactant, in a content of less than or equal to 15% by weight relative to the total weight of the cosmetic composition.

6. The cosmetic composition according to claim 5, wherein a content of fast volatile oil is greater than a content of slow volatile oil, which is greater than a content of non-volatile oil.

7. The cosmetic composition according to claim 1, wherein the pulverulent dyestuff is a mineral pigment and is present in a content ranging from 8% to 30% by weight relative to the total weight of the cosmetic composition.

8. The cosmetic composition according to claim 1, which is anhydrous.

9. The cosmetic composition according to claim 1, which is a water-in-oil (W/O) emulsion.

10. The cosmetic composition according to claim 1, wherein the lipophilic gelling agent is an organomodified clay.

11. The cosmetic composition according to claim 1, wherein the lipophilic gelling agent is a hydrophobic silica aerogel.

12. The cosmetic composition according to claim 11, wherein the hydrophobic silica aerogel has a specific surface area per unit of mass ($S_M$) ranging from 500 to 1500 m$^2$/g, and a size expressed as the volume-mean diameter (D[0.5]) ranging from 1 to 1500 μm.

13. The cosmetic composition according to claim 11, wherein the hydrophobic silica aerogel has an oil absorption capacity, measured at the wet point, ranging from 5 to 18 ml/g.

14. The cosmetic composition according to claim 11, wherein the hydrophobic silica aerogel has a tapped density ranging from 0.02 g/cm$^3$ to 0.10 g/cm$^3$.

15. The cosmetic composition according to claim 1, wherein the lipophilic gelling agent is present in the composition in an active material content ranging from 0.1% to 4% by weight, relative to the total weight of the cosmetic composition.

16. A cosmetic skin makeup process, comprising applying the cosmetic composition of claim 1 to the skin.

17. The cosmetic process according to claim 16, wherein the composition is applied to greasy skin and/or to skin that is subject to hot and/or humid atmospheric conditions.

* * * * *